United States Patent [19]

Hynes

[11] Patent Number: 4,594,358

[45] Date of Patent: Jun. 10, 1986

[54] ANALGESIC METHOD

[75] Inventor: Martin D. Hynes, Carmel, Ind.

[73] Assignee: Eli Lilly and Company, Indianapolis, Ind.

[21] Appl. No.: 705,177

[22] Filed: Feb. 25, 1985

[51] Int. Cl.$^4$ .......................................... A61K 31/135
[52] U.S. Cl. .................................................. 514/651
[58] Field of Search .......................................... 514/651

[56] References Cited

U.S. PATENT DOCUMENTS

| | | | |
|---|---|---|---|
| 4,035,511 | 7/1977 | Messing et al. | 424/330 |
| 4,083,982 | 4/1978 | Messing et al. | 424/260 |
| 4,313,896 | 2/1982 | Molloy et al. | 260/501.18 |
| 4,314,081 | 2/1982 | Molloy et al. | 564/347 |

OTHER PUBLICATIONS

Merck Index, 9th Ed (1976) pp. 1015-1016.
Hynes et al., *Drug Development Research*, 2, 33 (1982).
Messing et al., *Psychopharmacology Communications*, 1(5), 511 (1975).
Larson et al., *Life Sciences*, 21, 1807 (1977).
Sugrue et al., *J. Pharm. Pharmac.*, 28, 447 (1976).

*Primary Examiner*—Stanley J. Friedman
*Attorney, Agent, or Firm*—Robert A. Conrad; Arthur R. Whale

[57] ABSTRACT

This invention provides a method of producing analgesia in mammals which comprises administering dextropropoxyphene and fluoxetine or norfluoxetine. Pharmaceutical formulations useful in this method are also provided.

9 Claims, No Drawings

ANALGESIC METHOD

BACKGROUND OF THE INVENTION

Fluoxetine [3-(4-trifluoromethylphenoxy)-N-methyl-3-phenylpropylamine] has been shown to be a highly specific inhibitor of serotonin uptake. See Fuller et al., *J. Pharm. Exp. Ther.*, 193, 796 (1975) and Wong et al., id., 804 (1975). In addition, fluoxetine has been shown to possess analgesic properties when administered alone (U.S. Pat. No. 4,035,511) or when given with morphine (U.S. Pat. No. 4,083,982). Whether this latter activity is described as a synergistic effect or that of fluoxetine potentiating the morphine analgesic activity appears to depend upon the test system employed to demonstrate the analgesic activity. See Messing et al, *Psychopharmacology Comm.*, 1, 511 (1975); Sugrue et al., *J. Pharm. Pharmac.*, 28, 447 (1976); Larson et al., *Life Sci.*, 21, 1807 (1977); and Hynes et al., *Drug Dev. Res.*, 2, 33 (1982).

Norfluoxtine [3-(4-trifluoromethylphenoxy)-3-phenylpropylamine] is a metabolite of fluoxetine and is also known to block monoamine uptake, especially serotonin. See U.S. Pat. No. 4,313,896.

It is desirable to find methods of causing analgesia which result in few, if any, adverse side effects to the patient. Thus, a method of potentiating the analgesic effect of analgesics, such as dextropropoxyphene, would enable one to employ less dextropropoxyphene to achieve the desired analgesic effect while limiting side effects normally associated with higher doses of the analgesic.

SUMMARY OF THE INVENTION

This invention provides a method of potentiating dextropropoxyphene analgesia in mammals, either alone or in combination with aspirin or acetaminophen, which comprises the administration of an effective amount of fluoxetine or norfluoxetine prior to, concomitantly with, or after the administration of an amount of dextropropoxyphene which, if given alone, would produce less than the desired analgesic effect. This method is useful in that lower doses of dextropropoxyphene are required to produce analgesia thereby resulting in fewer undesired side effects, such as physical dependence, tolerance, and respiratory depression.

This invention also provides a pharmaceutical formulation comprising a combination of dextropropoxyphene and either fluoxetine or norfluoxetine or salts thereof, optionally in further combination with aspirin or acetaminophen. The formulations are useful for practicing the analgesic method described above.

DETAILED DESCRIPTION AND PREFERRED EMBODIMENTS

When used throughout this description, the terms "dextropropoxyphene," "fluoxetine," and "norfluoxetine" are meant to include not only the parent free base compounds, but also the recognized pharmaceutically acceptable acid addition salts of the respective compounds. Especially preferred salts of each compound are mineral acid salts such as the hydrochloride, sulfate, and phosphate salts and organic acid salts such as the napsylate salt. An especially preferred combination of compounds consists of dextropropoxyphene hydrochloride or napsylate together with fluoxetine hydrochloride.

The combination of fluoxetine or norfluoxetine and low doses of dextropropoxyphene is useful in four ways. First, the combination of fluoxetine or norfluoxetine and a dose of dextropropoxyphene that otherwise would not result in analgesia has been found to provide a useful analgesic effect. Second, the combination of fluoxetine or norfluoxetine and an analgesic dose of dextropropoxyphene can yield greater analgesia than the same dose of dextropropoxyphene alone. Third, the combination of dextropropoxyphene and fluoxetine or norfluoxetine results in analgesia even when there is tolerance to dextropropoxyphene alone. Finally, significant analgesia is seen for a longer period of time with a combination of dextropropoxyphene and fluoxetine as compared with either agent alone. The ability to employ lesser amounts of dextropropoxyphene than normally required to achieve the same analgesic effect is desirable in order to limit physical dependence, tolerance, and respiratory depression, as well as other adverse side effects normally associated with chronic administration of dextropropoxyphene. In addition, it is apparent that the combination provided by this invention is useful for producing analgesia even in patients who have become tolerant to opioids.

The ability of fluoxetine or norfluoxetine to potentiate the analgesic effect of dextropropoxyphene was demonstrated in the mouse writhing assay. Writhing, which is characterized by contraction of the abdominal musculature, extension of the hindlegs, and rotation of the trunk, was induced in albino male mice. The extent to which writhing is reduced following administration of a test compound is an indication of the analgesic activity of that compound.

Mice, weighing 18–24 grams, were fasted overnight and given the test compounds by gavage or subcutaneously. Writhing was then induced by the intraperitoneal administration of acetic acid (0.55 to 0.60 percent). Each treatment group consisted of five mice. The total number of writhes for the treatment group was determined during a 10-minute observation period starting five minutes after acetic acid administration. Control groups had a total of 40-60 writhes per mouse during the observation period. The results in the mouse writhing assay are presented either as the effective dose in mg/kg of the respective test compound required to inhibit induced writhing in the test animals by fifty percent ($ED_{50}$), or as the percent inhibition of writhing at the particular dose of the test compound administered.

In this test system, fluoxetine hydrochloride was found to be devoid of analgesic activity when administered at doses up to 160 mg/kg 30–180 minutes before writhing was induced. However, fluoxetine was found to potentiate an inactive dose of dextropropoxyphene napsylate in a manner that was dependent upon the dose of fluoxetine as summarized in Table 1. The oral administration of 10 mg/kg of dextropropoxyphene napsylate to a mouse 60 minutes prior to the assessment of writhing provided no inhibition of the writhing. However, when a 10, 20, or 40 mg/kg dose of fluoxetine hydrochloride was administered together with the dextropropoxyphene napsylate, inhibition of mouse writhing increased in a generally dose dependent and statistically significant manner. These data demonstrate that the combination of fluoxetine with a low dose of dextropropoxyphene, one that otherwise would not produce analgesia, provides significant analgesia in this test system.

TABLE 1

Fluoxetine Dose Dependently Potentiates an Inactive Dose of Dextropropoxyphene Napsylate

| Dextropropoxyphene Napsylate[1] (mg/kg) | Fluoxetine Hydrochloride[1] (mg/kg) | Percent Inhibition of Mouse Writhing |
|---|---|---|
| 10 | 0 | 0 |
| 10 | 10 | 22* |
| 10 | 20 | 46* |
| 10 | 40 | 32* |

[1]Fluoxetine hydrochloride and dextropropoxyphene napsylate were administered simultaneously by the oral route. Writhing was assessed 60 minutes later.
*Significantly different (p <0.05) from dextropropoxyphene napsylate alone by the Student's t test.

The $ED_{50}$ of dextropropoxyphene napsylate was determined to be 49.3 mg/kg in a second experiment when administered orally 60 minutes prior to assessment of writhing. As indicated in Table 2, the addition of 20 mg/kg of fluoxetine hydrochloride administered orally together with dextropropoxyphene napsylate provided an $ED_{50}$ almost 40% less than the control experiment where dextropropoxyphene napsylate was administered alone.

TABLE 2

Enhancement of Dextropropoxyphene Napsylate Analgesic Activity by Fluoxetine Hydrochloride

| Fluoxetine Hydrochloride[1] | Dextropropoxyphene Napsylate Inhibition of Mouse Writhing $ED_{50}$ (mg/kg) |
|---|---|
| 0 | 49.3 |
| 20 | 30.6 |

[1]Fluoxetine hydrochloride and dextropropoxyphene napsylate were administered simultaneously by the oral route. Writhing was assessed 60 minutes later.

The data presented in Table 3 show that when fluoxetine hydrochloride was administered orally three hours prior to the assessment of dextropropoxyphene napsylate analgesia, the $ED_{50}$ of dextropropoxyphene napsylate administered orally 30 minutes prior to the assessment of writhing was found to be half of that observed when saline was administered in place of the fluoxetine.

TABLE 3

Enhancement of Dextropropoxyphene Napsylate Analgesia in the Mouse Writhing Assay by Pretreatment with Fluoxetine Hydrochloride

| Pretreatment[1] | Dextropropoxyphene Napsylate Inhibition of Mouse Writhing $ED_{50}$ (mg/kg)[2] |
|---|---|
| Saline | 44.2 |
| Fluoxetine Hydrochloride (20 mg/kg) | 23.3 |

[1]Saline or fluoxetine hydrochloride was orally administered three hours prior to the assessment of dextropropoxyphene analgesia.
[2]Dextropropoxyphene napsylate was administered by the oral route 30 minutes prior to the assessment of writhing.

The concomitant administration of dextropropoxyphene and fluoxetine was also shown to increase dextropropoxyphene's analgesic effect over time. As summarized in Table 4, when the two compounds were orally administered simultaneously up to three hours before the assessment of writhing, the combination of 20 mg/kg of fluoxetine hydrochloride and 40 mg/kg of dextropropoxyphene napsylate provided a consistently greater analgesic effect compared to a control experiment where saline was administered in place of fluoxetine.

TABLE 4

Fluoxetine Increases Dextropropoxyphene's Analgesic Action Over Time in the Mouse Writhing Assay

| | Percent Inhibition of Writhing | |
|---|---|---|
| Minutes After Administration[1] | Dextropropoxyphene Napsylate 40 mg/kg + Saline | Dextropropoxyphene Napsylate 40 mg/kg + Fluoxetine Hydrochloride 20 mg/kg |
| 30 | 40 | 63* |
| 60 | 6 | 55* |
| 70 | 10 | 38* |
| 120 | 28 | 35 |
| 180 | 5 | 46* |

[1]Dextropropoxyphene napsylate and fluoxetine hydrochloride were administered simultaneously by the oral route.
*Significantly different (p <0.05) from dextropropoxyphene napsylate plus saline treatment.

Finally, a comparison of the $ED_{50}$ of dextropropoxyphene napsylate when administered subcutaneously 30 minutes prior to the assessment of mouse writhing was found to be twice the amount needed when 20 mg/kg of fluoxetine hydrochloride was concomitantly administered by the subcutaneous route as summarized in Table 5.

TABLE 5

Enhancement of Dextropropoxyphene Analgesia by Fluoxetine in the Mouse Writhing Assay

| Fluoxetine Hydrochloride[1] (mg/kg; s.c.) | Dextropropoxyphene Napsylate Induced Inhibition of Mouse Writhing $ED_{50}$ (mg/kg) |
|---|---|
| 0 | 9.95 |
| 20 | 4.97 |

[1]Dextropropoxyphene napsylate and fluoxetine hydrochloride were administered simultaneously by the subcutaneous route. Mouse writhing was assessed 30 minutes later.

The experiments summarized in Tables 2-5 clearly show that a combination of fluoxetine and an analgesic dose of dextropropoxyphene provide greater analgesia than dextropropoxyphene alone. Similarly, it is evident that in order to achieve the same analgesic effect, less dextropropoxyphene is required when fluoxetine is also administered.

The present invention provides a method of causing analgesia in mammals employing dextropropoxyphene in combination with either fluoxetine or norfluoxetine, optionally in combination with aspirin or acetaminophen. The method comprises administering the compounds by any number of routes including the oral, rectal, transdermal, subcutaneous, intravenous, intramuscular, or intranasal routes. The compounds are usually employed in the form of a pharmaceutical composition. The compounds may be administered individually at the same time or different times or together, and by the same route or by different routes. In a preferred embodiment, the compounds are administered orally and together. The potentiating effect of fluoxetine or norfluoxetine is observed when administered up to 24 hours prior to or 2 hours after the administration of dextropropoxyphene. A preferred regimen is the co-administration of both compounds. This co-administration can advantageously be accomplished by the administration of a pharmaceutical formulation comprising both compounds. Accordingly, this invention also provides a pharmaceutical composition comprising from about 1% to about 95% by weight of a mixture of dextropropoxyphene and either fluoxetine or norfluoxetine, optionally in further combination with aspirin or acetaminophen, associated with a pharmaceutically acceptable carrier, excipient, or diluent.

The ratio of the components by weight is preferably from about 1:1 to 1:4 fluoxetine/dextropropoxyphene. An especially preferred ratio is approximately 1:2 fluoxetine/dextropropoxyphene. The compositions are preferably formulated in a unit dosage form. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier. The preferred unit dosage forms of the present invention contain from about 10 to about 80 mg of fluoxetine or norfluoxetine and from about 30 to about 100 mg of dextropropoxyphene. In addition, the unit dosage form may contain up to 1000 mg of aspirin or acetaminophen, preferably 200-500 mg of aspirin or 325-650 mg of acetaminophen. However, it will be understood that the specific amount of compounds actually administered will be determined by a physician, in the light of the relevant circumstances including the chosen route of administration, the age, weight, and response of the individual patient, and the severity of the patient's symptoms, and therefore the above dosage ranges are not intended to limit the scope of the invention in any way.

In making the compositions of the present invention, the compounds will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. The compositions thus can be in the form of tablets, pills, powders, lozenges, sachets, cachets, elixirs, suspensions, emulsions, solutions, syrups, aerosols (as a solid or in a liquid medium), ointments containing for example up to 10% by weight of the active compounds, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl and propylhydroxybenzoates, talc, magnesium stearate and mineral oil. The formulations can additionally include lubricating agents, wetting agents, emusifying and suspending agents, preserving agents, sweetening agents or flavoring agents. The compositions of the invention may be formulated so as to provide quick, sustained or delayed release of all or any of the compounds after administration to the patient by employing procedures well known in the art.

The following examples are provided to further illustrate the formulations of this invention. The examples are illustrative only and are intended to limit the scope of the invention in any way.

EXAMPLE 1

Hard gelatin capsules are prepared using the following ingredients:

|  | Quantity (mg/capsule) |
|---|---|
| Fluoxetine hydrochloride | 60 |
| Dextropropoxyphene napsylate | 100 |
| Starch dried | 350 |
| Magnesium stearate | 10 |

The above ingredients are mixed and filled into hard gelatin capsules in 520 mg quantities.

EXAMPLE 2

A tablet formula is prepared using the ingredients below:

|  | Quantity (mg/tablet) |
|---|---|
| Norfluoxetine sulfate | 80 |
| Dextropropoxyphene sulfate | 25 |
| Aspirin | 325 |
| Cellulose, microcrystalline | 545 |
| Silicon dioxide, fumed | 20 |
| Stearic acid | 5 |

The components are blended and compressed to form tablets each weighing 1000 mg.

EXAMPLE 3

An aerosol solution is prepared containing the following components:

|  | Weight % |
|---|---|
| Fluoxetine | 0.18 |
| Dextropropoxyphene phosphate | 0.07 |
| Ethanol | 29.75 |
| Propellant 22 (Chlorodifluoromethane) | 70.00 |

The compounds are mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 4

| Tablets are made up as follows: | |
|---|---|
| Fluoxetine hydrochloride | 70 mg |
| Dextropropoxyphene Napsylate | 50 mg |
| Acetaminophen | 510 mg |
| Starch | 325 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 1000 mg |

The active ingredients, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 1000 mg.

EXAMPLE 5

| Capsules are made as follows: | |
|---|---|
| Fluoxetine sulfate | 20 mg |
| Dextropropoxyphene hydrochloride | 65 mg |
| Aspirin | 65 mg |
| Starch | 74 mg |
| Microcrystalline cellulose | 74 mg |
| Magnesium stearate | 2 mg |
| Total | 300 mg |

The active ingredients, cellulose, starch and magnesium stearate are blended, passed through a No. 45 mesh U.S. sieve, and filled into hard gelatin capsules in 300 mg quantities.

EXAMPLE 6

| Suppositories are made as follows: | |
|---|---|
| Fluoxetine phosphate | 80 mg |
| Dextropropoxyphene sulfate | 50 mg |
| Saturated fatty acid glycerides to | 2,000 mg |

The active ingredients are passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 7

| Suspensions are made as follows: | |
|---|---|
| Norfluoxetine hydrochloride | 70 mg |
| Dextropropoxyphene napsylate | 50 mg |
| Acetaminophen | 325 mg |
| Sodium carboxymethyl cellulose | 50 mg |
| Syrup | 1.25 ml |
| Benzoic acid solution | 0.10 ml |

| -continued | |
|---|---|
| Suspensions are made as follows: | |
| Flavor | q.v. |
| Color | q.v. |
| Purified water to | 5 ml |

The medicaments are passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

I claim:

1. A method of potentiating dextropropoxyphene analgesia in mammals which comprises the administration to said mammal of an effective amount of fluoxetine or norfluoxetine in the time range between 24 hours before and 2 hours after the administration of dextropropoxyphene.

2. The method of claim 1 wherein the compounds are administered simultaneously.

3. The method of claim 2 employing fluoxetine hydrochloride.

4. The method of claim 3 wherein about 10 to about 80 mg of fluoxetine hydrochloride and from about 30 to about 100 mg of dextropropoxyphene napsylate are administered.

5. A pharmaceutical formulation which comprises fluoxetine or norfluoxetine, dextropropoxyphene, and a pharmaceutically acceptable carrier, diluent, or excipient therefor, wherein the ratio of fluoxetine or norfluoxetine to dextropropoxyphene is about 4:1 to 1:4 and the combination of active ingredients is present in an effective amount.

6. A formulation according to claim 5 employing fluoxetine hydrochloride.

7. A formulation according to claim 6 wherein the ratio of fluoxetine hydrochloride to dextropropoxyphene is approximately 1:2.

8. A formulation according to claim 7 employing from about 10 to about 80 mg of fluoxetine hydrochloride and from about 30 to about 100 mg of dextropropoxyphene napsylate.

9. A formulation according to claim 8 which is formulated for oral administration.

* * * * *

UNITED STATES PATENT AND TRADEMARK OFFICE
CERTIFICATE OF CORRECTION

PATENT NO. : 4,594,358
DATED : June 10, 1986
INVENTOR(S) : Martin D. Hynes

It is certified that error appears in the above-identified patent and that said Letters Patent is hereby corrected as shown below:

Column 1, line 21, "Norfluoxtine" should read -- Norfluoxetine --.

Column 5, line 63, "are intended" should read -- are not intended --.

Signed and Sealed this

Twenty-third Day of February, 1988

Attest:

DONALD J. QUIGG

*Attesting Officer*  *Commissioner of Patents and Trademarks*